(12) United States Patent
Maki et al.

(10) Patent No.: US 7,794,939 B2
(45) Date of Patent: Sep. 14, 2010

(54) METHODS OF DNA METHYLATION DETECTION

(75) Inventors: Wusi Chen Maki, Coeur d'Alene, ID (US); Brian John Filanoski, Spokane, WA (US); Nirankar Mishra, Post Falls, ID (US); Shiva Rastogi, Post Falls, ID (US)

(73) Assignee: University of Idaho, Moscow, ID (US)

( * ) Notice: Subject to any disclaimer, the term of this patent is extended or adjusted under 35 U.S.C. 154(b) by 612 days.

(21) Appl. No.: 11/678,933

(22) Filed: Feb. 26, 2007

(65) Prior Publication Data

US 2009/0068649 A1    Mar. 12, 2009

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3

(58) Field of Classification Search .................... 435/6; 536/23.1, 24.3
See application file for complete search history.

(56) References Cited

U.S. PATENT DOCUMENTS

| | | | | | |
|---|---|---|---|---|---|
| 5,565,322 | A | * | 10/1996 | Heller | 435/6 |
| 5,605,662 | A | * | 2/1997 | Heller et al. | 422/68.1 |
| 5,854,033 | A | * | 12/1998 | Lizardi | 435/91.2 |
| 2006/0134657 | A1 | * | 6/2006 | Hodko et al. | 435/6 |
| 2008/0193931 | A1 | * | 8/2008 | Li et al. | 435/6 |
| 2008/0227652 | A1 | * | 9/2008 | Yamakawa | 506/9 |
| 2009/0068649 | A1 | * | 3/2009 | Maki et al. | 435/6 |
| 2009/0130659 | A1 | * | 5/2009 | Rehli | 435/6 |
| 2009/0191548 | A1 | * | 7/2009 | Berlin et al. | 435/6 |
| 2009/0197263 | A1 | * | 8/2009 | Nelson et al. | 435/6 |

OTHER PUBLICATIONS

Fisher et al., Characterization of cytosine methylated regions and 5-cytosine DNA methyltransferase (Ehmeth) in the protozoan parasite Entamoeba histolytica. Nucleic Acids Research 32(1) :287-297(2004).*
Maki et al., Nanowire-transistor based ultra-sensitive DNA methylation detection. Biosensors & Bioelectronics 23 : 780-787 (ePub Aug. 2007).*
Weber et al., Chromosome-wide and promoter-specific analyses identify sites of differential DNA methylation in normal and transformed human cells. Nature Genetics 37(8) : 253-262 (Aug. 2005).*
Laird, "The Power and the Promise of DNA Methylation Markers," Nature Reviews, Apr. 2003, vol. 3, pp. 253-265.
Riordan, et al., "Tetranitromethane. A Reagent for the Nitration of Tyrosine and Tyrosine and Tyrosyl Residues of Proteins," Journal of the American Chemical Society, Sep. 5, 1966, pp. 4104-4105.
Belinsky, et al., "Aberrant Promoter Methylation in Sputum and Serum for Lung Cancer Detection," Journal of Clinical Ligand Assay, vol. 25, No. 1, Spring 2002, pp. 95-99.
Egholm, et al., "PNA hybridizes to complementary oligonucleotides obeying the Watson-Crick hydrogen-bonding rules," Nature, vol. 365, Oct. 7, 1993, pp. 566-568.
Hashimoto, et al., "Preliminary evaluation of electrochemical PNA array for detection of single base mismatch mutations," The Royal Society of Chemistry, Lab on a Chip, 2001, 1, pp. 61-63.
Zheng, et al., "Multiplexed electrical detection of cancer markers with nanowire sensor arrays," Nature Biotechnology, vol. 23, No. 10, Oct. 2005, pp. 1294-1301.
Fritz, et al., "Electronic detection of DNA by its intrinsic molecular charge," PNAS, vol. 99, No. 22, pp. 14142-14146, (Oct. 2002).
Yan, et al., "Trans-HHS Workshop: Diet, DNA Methylation Processes and Health," "Applications of CpG Island Microarrays for High-Throughput Analysis of DNA Methylation," The Journal of Nutrition, Aug. 2002, 8S, Health Module, American Society for Nutritional Sciences, pp. 2430s-2434s.
Eads, MethyLight: a high-throughput assay to measure DNA methylation, Oxford University Pres, Nucleic Acids Research, 2000, vol. 28, No. 8, pp. 1-7.
Herman, "Methylation-specific PCR: A Novel PCR assay for methylation status of CpG islands," Proc. Natl. Acad. Sci. USA, vol. 93, Sep. 1996, Medical Sciences, pp. 9821-9826.
Costello, "Aberrant CpG-island methylation has non-random and tumour-type-specific patters," 2000 Nature America Inc. Nature Genetics, vol. 25, Feb. 2000, pp. 132-138.
Herman, et al., "Gene Silencing in Cancer in Association with Promoter Hypermethylation," N. Engl J. Med 349; 21, Nov. 20, 2003, pp. 2042-2054.
Kerman, et al., "Peptide Nucleic Acid-Modified Carbon Nanotube Field-Effect Transistor for Ultra-Sensitive Real-Time Detection of DNA Hybridization," NanoBiotechnology, vol. 1, 2005 Humana Press Inc., pp. 65-70.
Hou, et al., "Detection of methylation of human p16ink4a gene 5'-CpG islands by electrochemical method coupled with linker-PCR," Nucleic Acids Research, vol. 31 No. 16, Oxford University Press 2003, e92, pp. 1-7.

* cited by examiner

*Primary Examiner*—Ethan Whisenant
(74) *Attorney, Agent, or Firm*—Howard Eisenberg, Esq.

(57) ABSTRACT

The present invention provides for methods of DNA methylation detection. The present invention provides for methods of generating and detecting specific electronic signals that report the methylation status of targeted DNA molecules in biological samples.

Two methods are described, direct and indirect detection of methylated DNA molecules in a nano transistor based device. In the direct detection, methylated target DNA molecules are captured on the sensing surface resulting in changes in the electrical properties of a nano transistor. These changes generate detectable electronic signals. In the indirect detection, antibody-DNA conjugates are used to identify methylated DNA molecules. RNA signal molecules are generated through an in vitro transcription process. These RNA molecules are captured on the sensing surface change the electrical properties of nano transistor thereby generating detectable electronic signals.

8 Claims, 5 Drawing Sheets

METHODS OF DNA METHYLATION DETECTION

GOVERNMENT SUPPORT

This invention was funded in part by NASA Grant No. NNG06GB45G; HUD Grant No. B02SPID0181 and USDA CSREES Grant No. 3447916054.

FIELD OF INVENTION

The present invention relates to methods for the detection of methylated DNA molecules. More specifically, the present invention relates to methods for the detection of DNA methylation in a nano electronic device.

BACKGROUND

Early detection is one of the most challenging issues in cancer diagnosis. Currently, diagnosis depends on a variety factors including illness symptoms, the detection of biomarkers in blood and/or body fluids, the microscopic analysis of biopsy samples, as well as imaging technology. Limited sensitivity in these methods and technologies can result in the delay of treatment. The National Cancer Institute has indicated there is an urgent need of new technologies for cancer early diagnosis.

Cancer is known as a disease driven by genetic abnormalities. Recently, however, research has suggested that epigenetic alterations of gene function may also be central to the pathogenesis of this disease. Epigenetic alterations include heritable changes in the gene expression that are not caused by direct alteration of the gene's nucleotide sequence. Abnormal DNA methylation at gene transcription sites can result in epigenetic silencing of genes that protect against tumor formation or that repair DNA. Research into gene silencing has focused on the regions of high CpG content, known as CpG islands. CpG islands are often located near gene transcription sites. In normal cells, most promoter-associated CpG islands are unmethylated. But in cancer cells, promoter region CpG islands are most likely to be methylated. Thus, the detection of promoter methylation in tumor suppress genes is one of most important assays in early cancer diagnosis. Conventional methods for DNA methylation detection use methylation specific and/or methylation sensitive restriction enzymes for restriction landmark analysis. Recently, several advanced methods have been developed for DNA methylation detection, including bisulfite sequencing, methylation-specific PCR, MethyLight, CpG island microarray. However, major drawback with these methods include complicated procedures, relatively low sensitivity, time consuming and false positive. Therefore, the development of new technologies to improve DNA methylation detection will have a significant impact in early cancer detection.

The $p16^{INK}$ promoter was chosen as a target of the detection model, since its protein inhibits cell cycle progression. Methylation of CpG islands in p16 promoter and the first exon regions inactivates transcription of the p16 gene. This is significantly associated with lung cancer. Recently, field effect transistor (FET) based electronic charge detectors were introduced into DNA detection by several research groups. However, using charge detector to report DNA methylation events is a challenge, since both methylated and unmethylated DNA carry the same amount of electrical charge. In light of the foregoing there is a need for a DNA methylation detection system that has increased sensitivity yet is relatively easy to operate and without the need for bisulfite treatment or PCR amplification.

SUMMARY OF INVENTION

Accordingly, the present invention is directed to methods of detecting of DNA methylation in biological samples that is based on nano-transistor based electronic detection, which is label free, no requirement of bisulfite treatment and PCR amplification Additional features and advantages of the invention will be set forth in the description which follows, and in part will be apparent from the description, or may be learned by practice of the invention. The objectives and other advantages of the invention will be realized and attained by the method particularly pointed out in the written description and the claims hereof as well as the appended drawings.

To achieve these and other advantages and in accordance with the purpose of the invention, as embodied and broadly described, one object of the present invention is to provide a direct method of DNA methylation detection. In this direct method of DNA methylation detection is accomplished by exposing the DNA molecules from a biological sample to D-desthiobiotin labeled sequence specific probe, allowing hybridization thereby creating a target DNA; capturing the hybridized target DNA molecules with the nitro-streptavidin magnetic beads; removing unhybridized DNA and D-desthiobiotin molecules by washing; eluting the captured DNA molecules from the nitro-streptavidin magnetic beads using D-biotin; capturing the target DNA molecules with a monoclonal anti-methylcytosine antibody immobilized on a sensing surface of an electronic device; and sensing in the presence of methylated target DNA molecules by detecting the changed electrical properties of the sensing surface thereby generating a signal.

Another object of the present invention related to an indirect method DNA methylation detection. In this method, DNA methylation detection is accomplished by hybridizing DNA molecules from a biological sample with biotin-labeled sequence specific probes; capturing the DNA-biotin-labeled sequence probes with streptavidin magnetic beads; exposing the captured DNA-biotin-labeled sequence probes to a conjugate of monoclonal anti-5-methylcytosine antibody thereby creating a DNA template; generating RNA molecules from the DNA template by an in vitro transcription process; capturing the RNA molecules by peptide nucleic acids immobilized on a sensing surface of an electronic device through a hybridization process; generating an electronic signal changing the electronic properties of the sensing surface in the presence of captured RNA molecules.

In both methods the electronic signal is detected in an electronic device by a nano transistor, or other basic electronic device It is to be understood that both the following forgoing general description and the following detailed description are exemplary and explanatory and are intended to provide further explanation of the invention as claimed.

The accompanying figures are included to provide a further understanding the invention and are incorporated and constitute a part of this specification, illustrate several embodiments of the present invention and together with the description serve to explain the principals of the invention.

DETAILED DESCRIPTION

Reference will now be made in detail to the present preferred embodiments of the invention, examples of which are illustrated in the accompanying figures.

Two methods described in this invention teach the generation of methylation specific signals that can be detected on a nano transistor based device. The detection sensitivity has been achieved at atom mole level.

Figure 1:
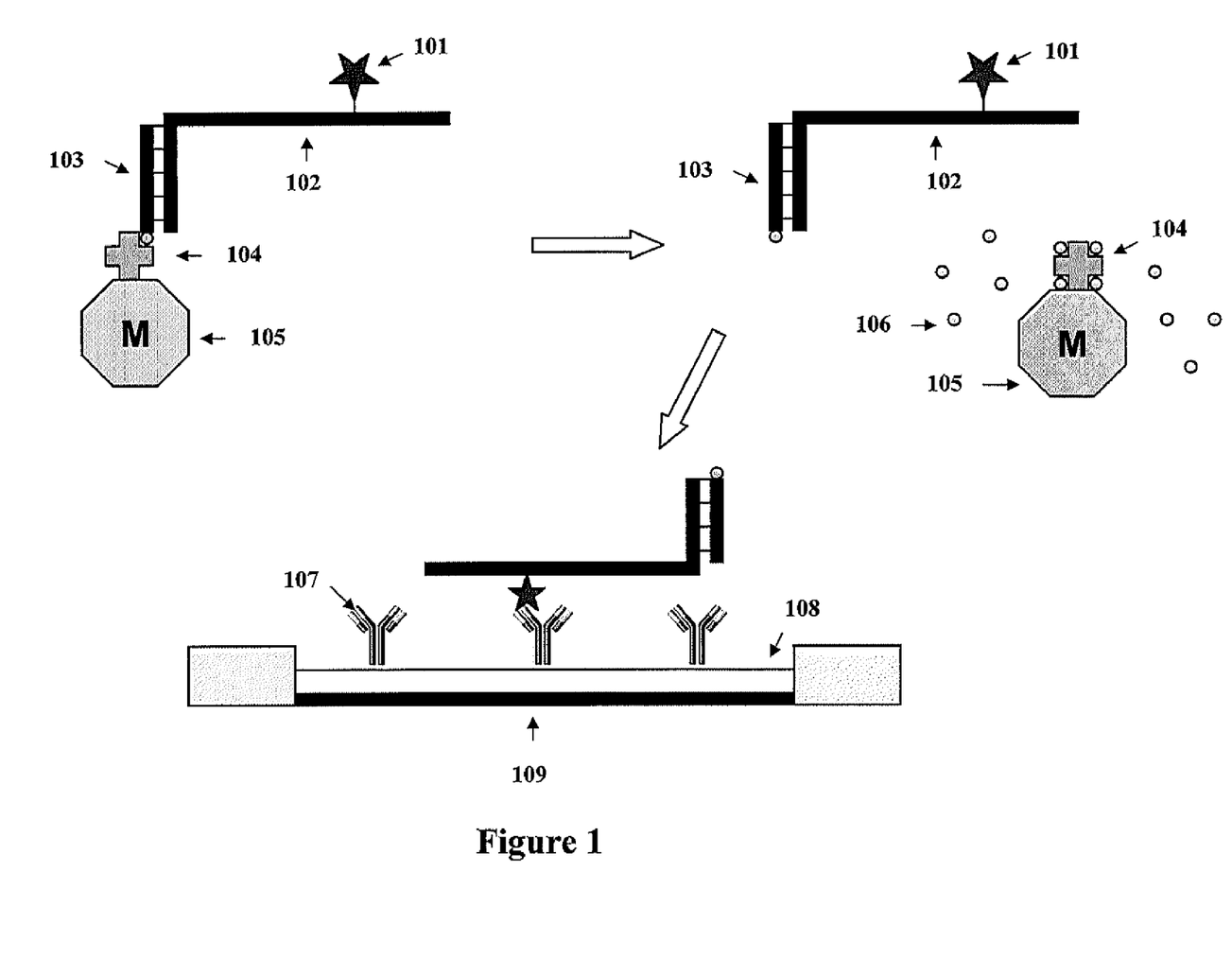
FIG. 1 is a schematic diagram depicting the method of direct DNA methylation detection.

An exemplary embodiment of the direct DNA methyation detection method is shown in FIG. 1. FIG. 1 is a diagram of the direct detection of DNA methylation method. Methylated 101 and non-methylated (not shown) target DNA molecules 102, are hybridized with a D-desthiobiotinlated specific probe 103, then these hybridized target DNA-D-desthiobiotinlated molecules are captured using nitro-streptavidin 104 magnetic beads 105. After washing away any unbound DNA and D-desthiobiotinlated specific probe molecules, D-biotin 106 is used to elute capture DNA molecules 102 from nitro-streptavidin 104. Those of ordinary skill in the art will readily understand that D-desthiobiotin and D-biotin can be other haptens or tags. Similarly, the nitro-streptavidin and streptavidin can be any biomolecules that recognize haptens or tags and the magnetic beads may be any solid material that can be separated from the liquid phase. Methylated 101 target DNA molecules 102 are captured by monoclonal anti-methylcytostine antibody 107 immobilized on the sensing surface 108 of a nano-transistor 109. Non-methylated target DNA molecules (not shown) are washed away. Methylated 101 target DNA molecules 102 are detected by changing electrical properties of the sensing surface 108.

Figure 2:
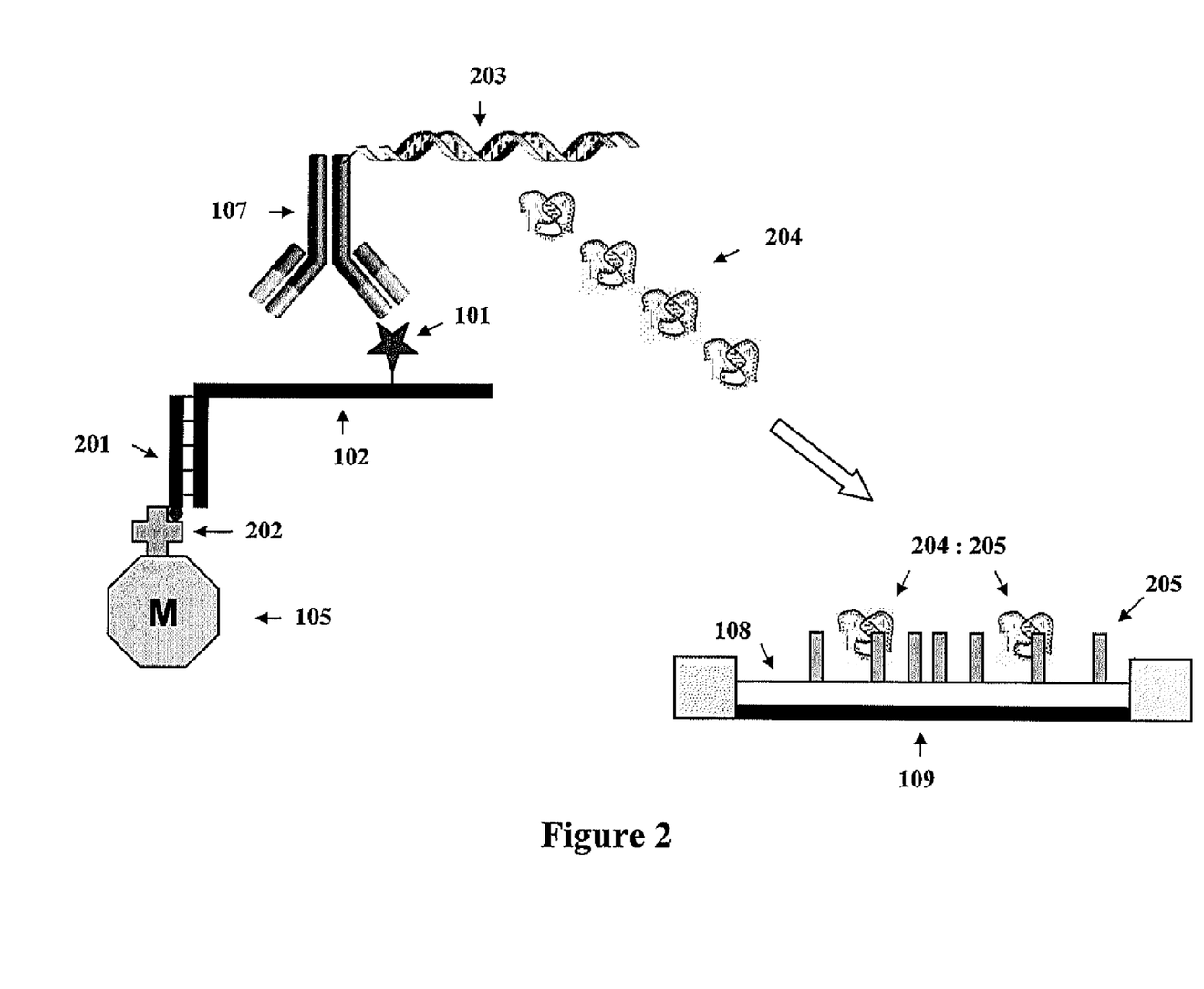
FIG. 2 is a schematic diagram depicting the method of indirect DNA methylation detection.

Turning now to FIG. 2, which is a diagram of the indirect detection of DNA methylation method. In this embodiment, methylated 101 and non-methylated (not shown) target DNA molecules 102, are hybridized with a biotinylated specific probe 201, are captured by streptavidin 202 magnetic beads 105. Monoclonal anti-methylcytosine antibody 107 conjugated with a DNA template 203 binds to methylated cytosine 101. RNA signal molecules 204 are generated through in vitro transcription. RNA molecules 204 are captured by their complimentary PNA molecules 205 immobilized on the sensing surface 108 of nano-transistor 109, and detected by changing electrical properties of the sensing surface. It will be readily apparent to one of ordinary skill in the art that the conjugate can be antibody-beads with oligonucleotides which in turn are captured by PNA on the sensing surface. Similarly, the peptide nucleic acid can be other biomolecules capable of recognizing and capturing RNA or any oligonucleotide.

Figure 3:
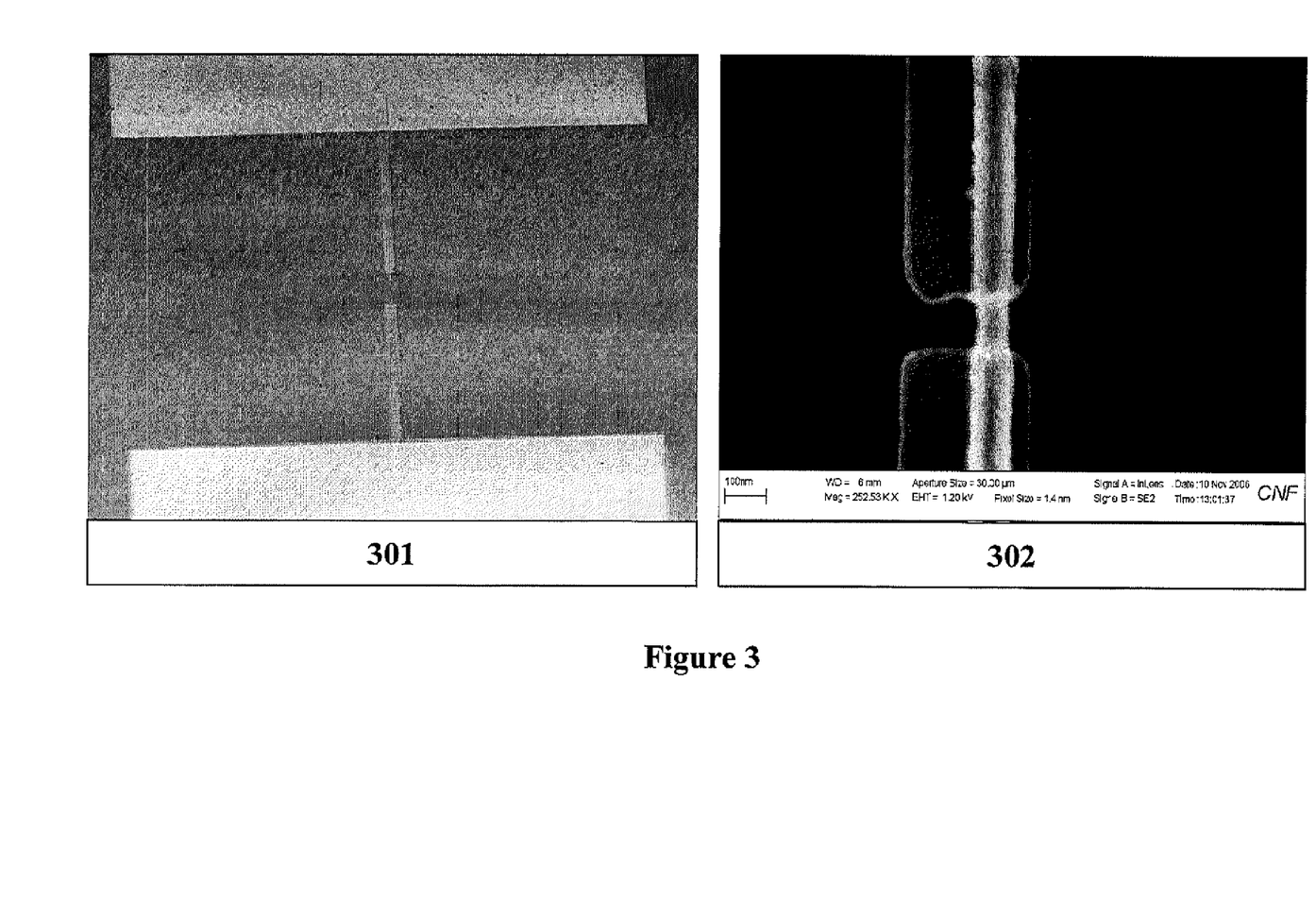
FIG. 3 is photomicroscopic image of nano transistor.

Looking now at FIG. 3, which is a photomicroscopic images of a nano transistor. Image 301 is an image of the nano transistor captured on Olympus B60 microscope under darkfield-reflected light using a 20× material objective. Image 302 is the image of low doped semiconductor nanowire and this image was taken at the Cornell Nanoscale Facility using a scanning electron micrograph at a Magnification of 252KX and 1.2 kV EHT.

Figure 4:
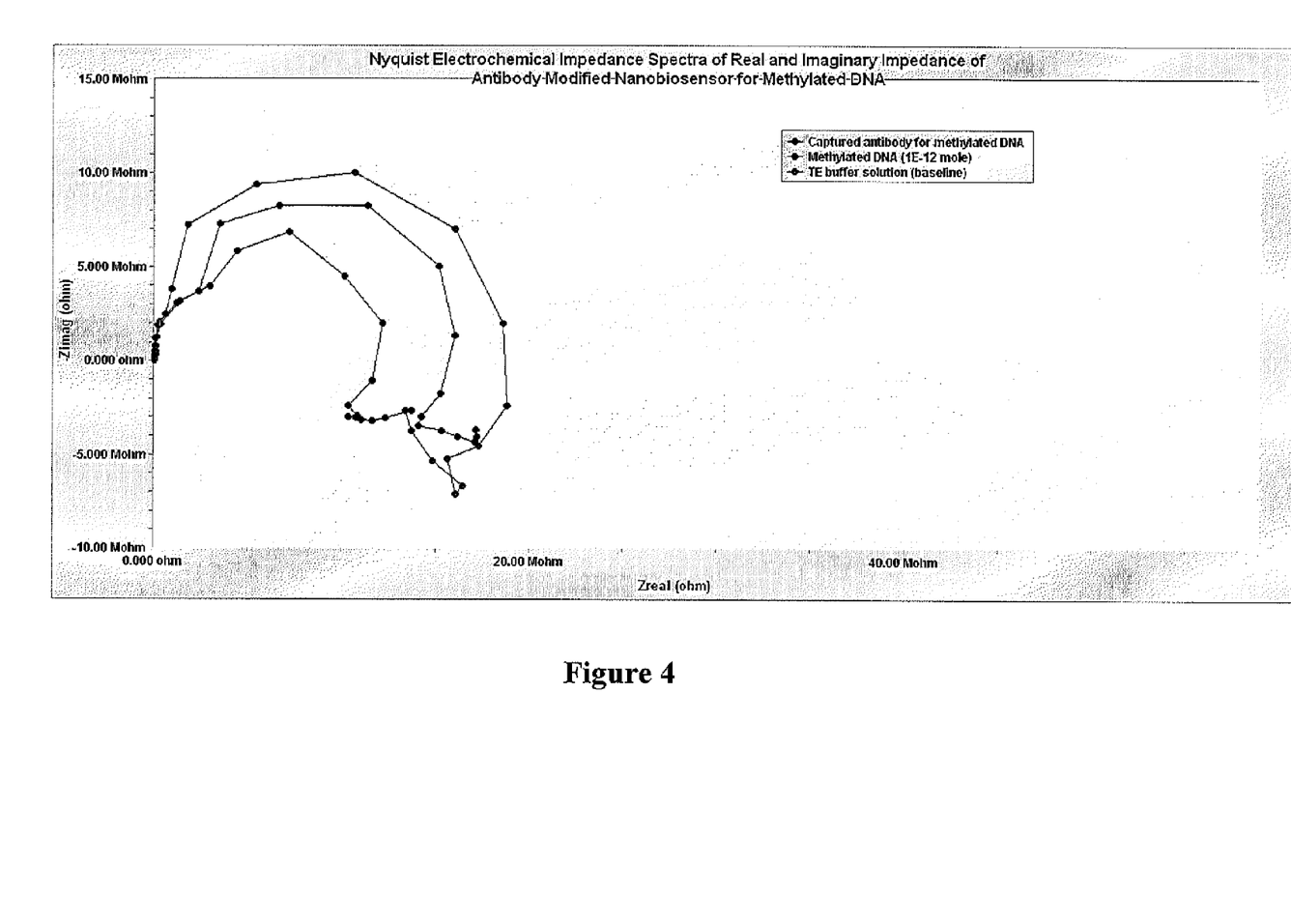
FIG. 4 is a spectra of electronic detection of DNA methylation by using the direct detection method.

Turning now to FIG. 4 which is a spectra of the electronic detection of DNA methylation by using direct detection method. To generate these spectra, a 1 µl sample containing one (1) picomole of methylated p16 promoter DNA molecules was used as a target in the experiment. DNA sample was loaded onto the anti-methylcytosine antibody modified sensing surface, and incubate for 15 minutes. Unbound DNA molecules were washed away by using TE buffer. Bound DNA molecules were detected as shown in the spectra.

Figure 5:
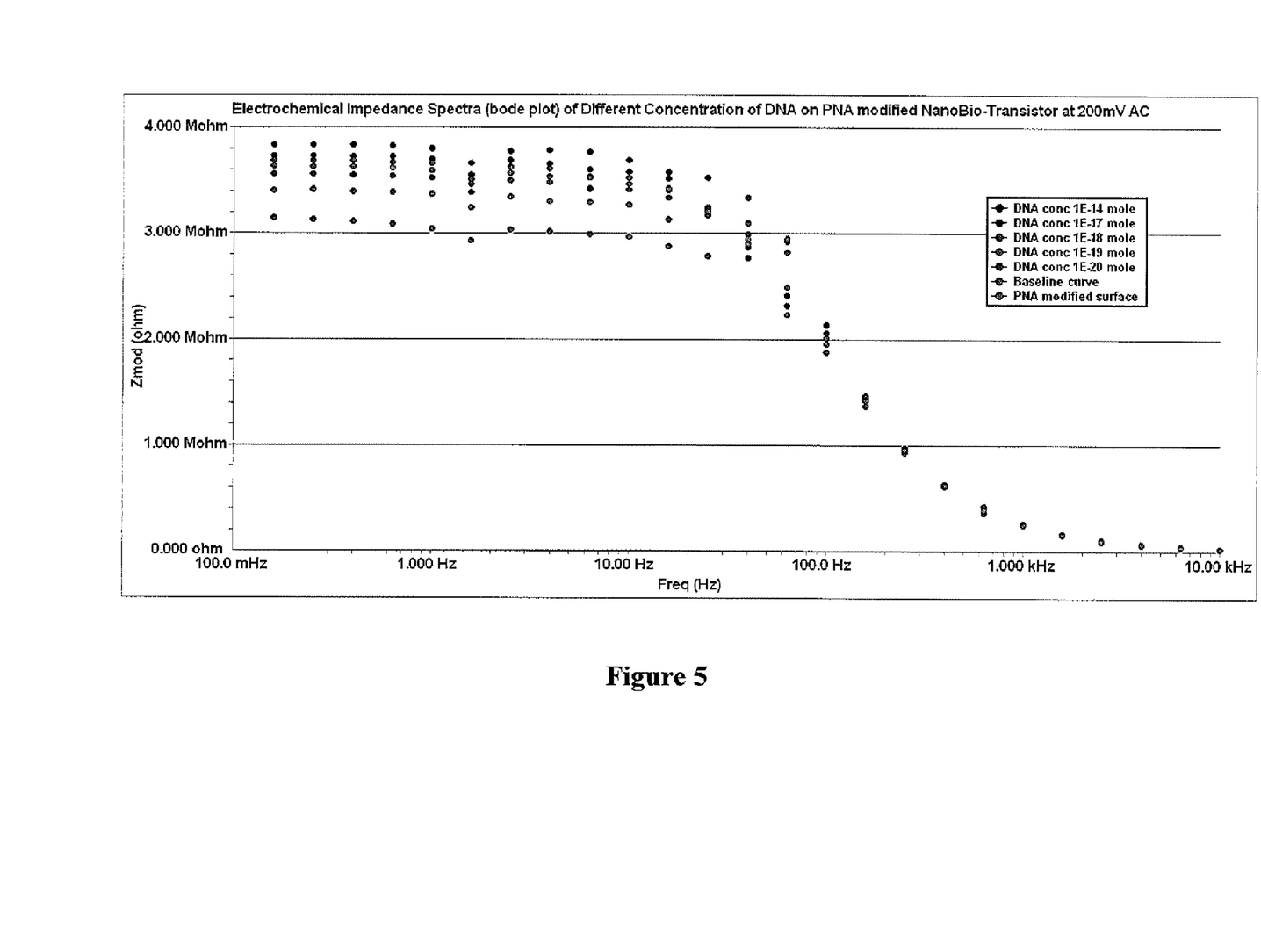
FIG. 5 is a spectra of electronic detection of DNA methylation by using the indirect detection method.

Turning now to FIG. 5 which is a spectra of electronic detection of DNA methylation by using the indirect detection method. To generate these spectra, a serial dilution of oligonucleotide A20 was made in TE buffer. Experiments were performed on the same nano transistor with PNA modified sensing surface. A 0.5 µl of sample containing $1 \times 10^{-12}$ to $10^{-20}$ mole oligonucleotide A20 was loaded onto the sensing surface in the tests. Hybridization was performed at room temperature for 15 minutes. Unbound oligonucleotides were washed away by using TE buffer. Hybrids were detected as shown in the spectra.

```
                                          (SEQ ID NO: 1)
P16 promoter region target sequence
5' ACCAGAGGGTGGGGCGGACCGCGTGCGCTCGGCGGCTGCGGAGAGGG

GGAGAGCAGGCAGCGGGCGGCGGGGAGCAGCATGGAGCCGGCGGCGGGGA

GCA 3'
                                          (SEQ ID NO: 2)
Top strand oligonucleotide
(partial target sequence)
5' ACC AGA GGG TGG GGC GGA CCG CGT GCG CTC GGC GGC TGC GGA GAG GGG GAG AGC AGG CAG C 3'
                                          (SEQ ID NO: 3)
Bottom strand oligonucleotide
(partial target sequence)
5' TGC TCC CCG CCG CCG GCT CCA TGC TGC TCC CCG CCG

CCC GCT GCC TGC TCT CCC 3'
```

Overlap 15 bases, Tm=56.2

Probes

```
                                          (SEQ ID NO: 4)
  5' Amine-TGC TCC CCG CCG CCG GCT CCA TGC 3'
```

D-Desthiobiotin labeling procedure was performed according to the product information sheet from Molecular Probes (Invitrogene).

```
                                          (SEQ ID NO: 5)
  5' Biotin-TGC TCC CCG CCG CCG GCT CCA TGC 3'
```

DNA Template for Antibody Conjugation

```
                                          (SEQ ID NO: 6)
5' Thio-GGT AAT ACG ACT CAC TAT AGG GAA AAA AAA AAA AAA AAA AA 3'
T7 promoter sequence is under lined.
```

Chemical Structure of a PNA Oligomer and RNA (B is Base)

Nitro-streptavidin was prepared according to the published procedure as detailed by Laird P W and by Riodan, J. F., Sokolovsky, M. and Valee, B. L, hereby incorporated by reference in its entirety.

EXAMPLE 1

1. Target DNA Preparation and Methylation

To generate a full length of target DNA, annealing and extension of top and bottom strands oligonucleotides were performed. DNA polymerase Klenow fragment exo⁻ was used for the strand extension. Methylation of target DNA was performed by using DNA methylation kit from New England Biolab. Purification of methylated DNA was performed through phenol extraction and ethanol precipitation procedures.

2. Antibody-DNA Conjugation

Antibodies were modified with bifunctional linker LC-SMCC (Pierce) and purified by using P-6 spin column. Sulfonated DNA template was reduced by using DTT and purified by using P-6 spin column. Modified antibody and reduced DNA template were then mixed together at 1:4 ratio. Conjugation reaction was carried out over night. Conjugates were purified by using P-100 gravity flow column. The biological function of the conjugates was tested by antibody antigen reaction and in vitro transcription.

3. Synthesis and Characterization of PNA

PNAs were synthesize using Boc/Z or Fmoc/Bhoc protected monomers is described using manual and automated solid phase synthesis protocol as describe by Leif Christensen, Richard Fitzpatrick and Rolf H. Berg, Chemical synthesis of Boc/Z and Fmoc/Bhoc PNA monomers using solution phase chemistry is reported. PNA monomers, reagents and wash solution for PNA synthesis are commercially available through ASM Research Chemicals e.K. Germany. PNA products were released from the solid support and analyzed for purity by reverse phase HPLC and MALDI-TOF mass spectroscopy.

4. Sensing Surface Modification

The sensing surface was cleaned by plasma treatment and sonication. A mixture of MUA/MPA was used to functionize the surface with COOH groups. A mixture of EDAC/NHS was used as activated linker for covalently linking antibody or peptide nucleic acid on the sensing surface. Modified surface was blocked by PBS with 1 mM PEG, 1 mM glycine and 0.01% HSA.

5. Methylation DNA Detection

The principle of direct and indirect detection of methylated DNA was presented in FIGS. 1 and 2. The results of electronic detection were presented in FIGS. 4 and 5. Non-methylated DNA with identical sequence was used as negative control in both detection models.

The invention claimed is:

1. A method of detecting DNA methylation in a biological sample comprising:

a) targeting DNA molecules hybridized with hapten-labeled sequence specific probes to produce DNA-hapten-labeled sequence probes;

b) capturing the DNA-hapten-labeled sequence probes with a hapten recognizing biomolecule on solid material;

c) exposing the captured DNA-hapten-labeled sequence probes to a conjugate of antibody and a DNA template, or a conjugate of antibody and a particle with oligonucleotides;

d) generating RNA molecules from the DNA template by an in vitro transcription process, or releasing oligonucleotides from the particle;

e) capturing RNA molecules or oligonucleotides by nucleic acid recognizing biomolecules immobilized on a sensing surface of an electronic device through a hybridization process;

f) changing the electronic properties of the sensing surface by the presence of RNA molecules or oligonucleotides, thereby generating electronic signals; and g) detecting the generated electronic signals by an electronic signal detector, thereby detecting DNA methylation in the biological sample.

2. The method according to claim 1, wherein the hapten is D-biotin.

3. The method according to claim 1, wherein the hapten-recognizing biomolecule is nitro-streptavidin or streptavidin.

4. The method according to claim 1, wherein the solid material is magnetic beads.

5. The method according to claim 1, wherein the antibody is monoclonal anti-5-methylcytosine.

6. The method according to claim 1, wherein the particle is a nano-gold particle.

7. The method according to claim 1, wherein the nucleic acid recognizing biomolecule is peptide nucleic acid.

8. The method according to claim 1 wherein the electronic signal detector is a nano transistor, or other basic electronic device.

* * * * *

SEQUENCE LISTING

<160> NUMBER OF SEQ ID NOS: 6

<210> SEQ ID NO 1
<211> LENGTH: 101
<212> TYPE: DNA
<213> ORGANISM: Homo sapiens

<400> SEQUENCE: 1
accagagggt ggggcggacc gcgtgcgctc ggcggctgcg gagaggggga gagcaggcag      60

```
cgggcggcgg ggagcagcat ggagccggcg ggcggggagc a                 101

<210> SEQ ID NO 2
<211> LENGTH: 61
<212> TYPE: DNA
<213> ORGANISM: Homo sapiens

<400> SEQUENCE: 2
accagagggt ggggcggacc gcgtgcgctc ggcggctgcg gagagggggga gagcaggcag   60 c                                                                   61

<210> SEQ ID NO 3
<211> LENGTH: 54
<212> TYPE: DNA
<213> ORGANISM: Homo sapiens

<400> SEQUENCE: 3
tgctccccgc cgccggctcc atgctgctcc ccgccgcccg ctgcctgctc tccc           54

<210> SEQ ID NO 4
<211> LENGTH: 24
<212> TYPE: DNA
<213> ORGANISM: artificial
<220> FEATURE:
<223> OTHER INFORMATION: Synthetic DNA

<400> SEQUENCE: 4
tgctccccgc cgccggctcc atgc                                           24

<210> SEQ ID NO 5
<211> LENGTH: 24
<212> TYPE: DNA
<213> ORGANISM: Artificial
<220> FEATURE:
<223> OTHER INFORMATION: synthetic DNA

<400> SEQUENCE: 5
tgctccccgc cgccggctcc atgc                                           24

<210> SEQ ID NO 6
<211> LENGTH: 44
<212> TYPE: DNA
<213> ORGANISM: artificial
<220> FEATURE:
<223> OTHER INFORMATION: synthetic DNA

<400> SEQUENCE: 6
ggtaatacga ctcactatag ggaaaaaaaa aaaaaaaaaa aaaa                     44
```